United States Patent [19]

Lewis et al.

[11] Patent Number: 5,482,034

[45] Date of Patent: Jan. 9, 1996

[54] METHOD AND APPARATUS FOR SPECTROPHOTOMETRIC CEREBRAL OXIMETRY AND THE LIKE

[75] Inventors: Gary D. Lewis, Grosse Pointe Farms, Mich.; Hugh F. Stoddart, Groton, Mass.

[73] Assignee: Somanetics Corporation, Troy, Mich.

[21] Appl. No.: 297,425

[22] Filed: Aug. 29, 1994

Related U.S. Application Data

[63] Continuation of Ser. No. 69,096, May 28, 1993, abandoned.

[51] Int. Cl.$^6$ .................................................. A61B 5/00
[52] U.S. Cl. .......................... 128/633; 128/664; 356/41
[58] Field of Search ..................... 128/633.4, 664–667; 356/35–41

[56] References Cited

U.S. PATENT DOCUMENTS

| | | | |
|---|---|---|---|
| 2,790,438 | 4/1957 | Paplin et al. ........................... | 28/633 |
| 3,230,951 | 1/1966 | Teschner ................................ | 128/666 |
| 3,602,213 | 8/1971 | Howell et al. ......................... | 128/633 |
| 3,769,974 | 11/1973 | Smart et al. . | |
| 3,810,460 | 6/1974 | Van Nie ................................. | 128/666 |
| 3,814,081 | 6/1974 | Mori ...................................... | 128/2 L |
| 3,822,695 | 7/1974 | Takayama .............................. | 128/2 L |
| 3,910,701 | 10/1975 | Henderson et al. .................... | 128/625 |
| 4,013,067 | 3/1977 | Kresse et al. . | |
| 4,015,595 | 4/1977 | Benjamin, Jr. ......................... | 128/2.05 V |
| 4,063,551 | 12/1977 | Sweeney . | |
| 4,091,803 | 5/1978 | Pinder .................................... | 128/2.05 P |
| 4,109,643 | 8/1978 | Bond et al. ............................ | 128/2 L |
| 4,163,447 | 8/1979 | Orr ......................................... | 128/666 |
| 4,223,680 | 9/1980 | Jobsis .................................... | 128/633 |
| 4,249,540 | 2/1981 | Koyama et al. ....................... | 128/666 |
| 4,259,963 | 4/1984 | Huch ..................................... | 128/635 |
| 4,267,844 | 5/1981 | Yamanishi ............................. | 128/633 |
| 4,281,645 | 8/1981 | Jobsis .................................... | 128/633 |
| 4,321,930 | 3/1982 | Jobsis et al. ........................... | 128/633 |
| 4,332,258 | 6/1982 | Arai et al. .............................. | 128/666 |
| 4,336,809 | 6/1982 | Clark ..................................... | 128/665 |
| 4,344,438 | 8/1982 | Schultz .................................. | 128/634 |

(List continued on next page.)

FOREIGN PATENT DOCUMENTS

| | | | |
|---|---|---|---|
| 2517129 | 6/1976 | Germany ............................... | 356/32 |
| 2076963A | 12/1981 | United Kingdom ................... | 128/2 L |
| WO8909566 | 10/1989 | WIPO . | |

*Primary Examiner*—Angela D. Sykes
*Assistant Examiner*—Robert L. Nasser, Jr.
*Attorney, Agent, or Firm*—Price, Heneveld, Cooper, DeWitt & Litton

[57] ABSTRACT

Spectrophotometric apparatus and related methodology, including a sensor having a source and at least two receivers of electromagnetic radiation such as red and/or near-infrared light, which is applied non-invasively to the outer periphery of a patient or other animate test subject to examine a particular internal region to which is disposed beyond a peripheral extremity of specifically indeterminate thickness lying immediately inwardly of the outer periphery of the test subject. The location of the source and detectors test are selected to be at points spaced from one another by unequal first and second distances defining first and second mean optical paths of specifically differing length, with the second such path defining a primary internal area containing the particular region to be examined, the first optical path generally defining a second internal area located in the primary internal area but substantially separate from the particular internal region to be examined, and the first such optical path including the full thickness of a predetermined typical such peripheral extremity plus at least a small portion of the physiological substance immediately therebeyond. Signals are produced which are representative of the radiation detected by the first and second receivers, and such signals are processed to obtain data which particularly characterizes selected attributes of the substance within the particular internal region, substantially without effects attributable to the secondary internal volume, The second receiver is preferably disposed about thirty to forty millimeters from the source, and the first receiver positioned not closer than about twenty millimeters therefrom.

21 Claims, 3 Drawing Sheets

U.S. PATENT DOCUMENTS

| | | | |
|---|---|---|---|
| 4,350,163 | 9/1982 | Ford, Jr. et al. | 128/633 |
| 4,380,240 | 4/1983 | Jobsis et al. | 128/633 |
| 4,510,938 | 4/1985 | Jobsis et al. | 128/633 |
| 4,515,165 | 5/1985 | Carroll | 128/664 |
| 4,570,638 | 2/1986 | Stoddart et al. | 128/665 |
| 4,685,464 | 3/1987 | Goldberger et al. | 128/633 |
| 4,770,179 | 10/1988 | New, Jr. et al. | 128/633 |
| 4,805,623 | 2/1989 | Jobsis | 128/633 |
| 4,819,752 | 4/1989 | Zelin | 128/633 |
| 4,825,872 | 5/1989 | Tan et al. | 128/633 |
| 4,825,879 | 5/1989 | Tan et al. | 128/633 |
| 4,830,014 | 5/1989 | Goodman et al. | 128/665 |
| 4,840,179 | 6/1989 | Ullrich | 128/633 |
| 4,865,038 | 9/1989 | Rich et al. | 128/633 |
| 4,867,557 | 9/1989 | Takatami et al. | 356/41 |
| 4,880,304 | 11/1989 | Jaeb et al. | 356/41 |
| 4,928,691 | 5/1990 | Nicolson et al. | 128/633 |
| 4,938,218 | 7/1990 | Goodman et al. | 128/633 |
| 4,964,408 | 10/1990 | Hink et al. | 128/633 |
| 5,057,695 | 10/1991 | Hirao et al. | 128/633 X |
| 5,080,098 | 1/1992 | Willett | 128/633 |
| 5,094,240 | 3/1992 | Muz | 128/633 |
| 5,111,817 | 5/1992 | Clark et al. | 128/633 |
| 5,139,025 | 8/1992 | Lewis et al. | 128/665 |
| 5,140,989 | 8/1992 | Lewis et al. | 128/633 |
| 5,217,013 | 6/1993 | Lewis et al. | 128/633 |
| 5,285,784 | 2/1994 | Seeker | 128/633 |

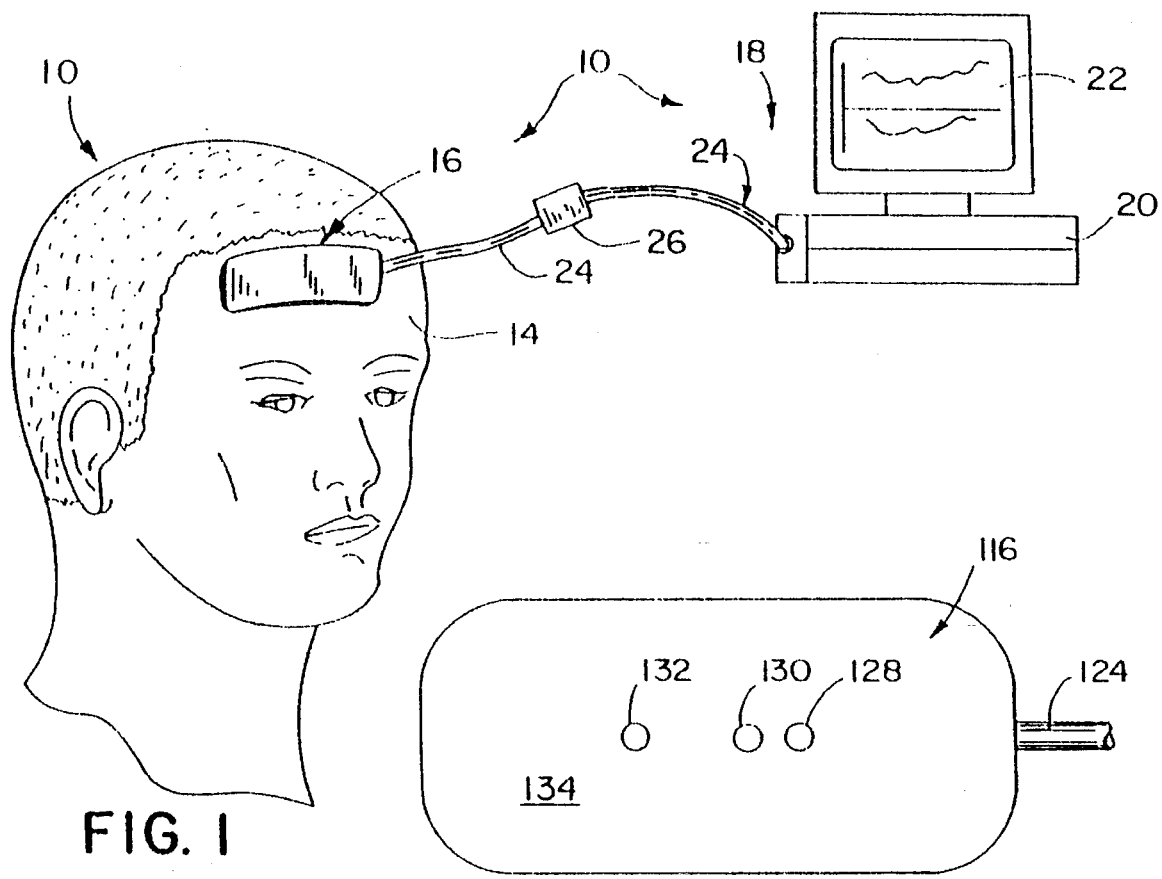
FIG. 1
FIG. 2
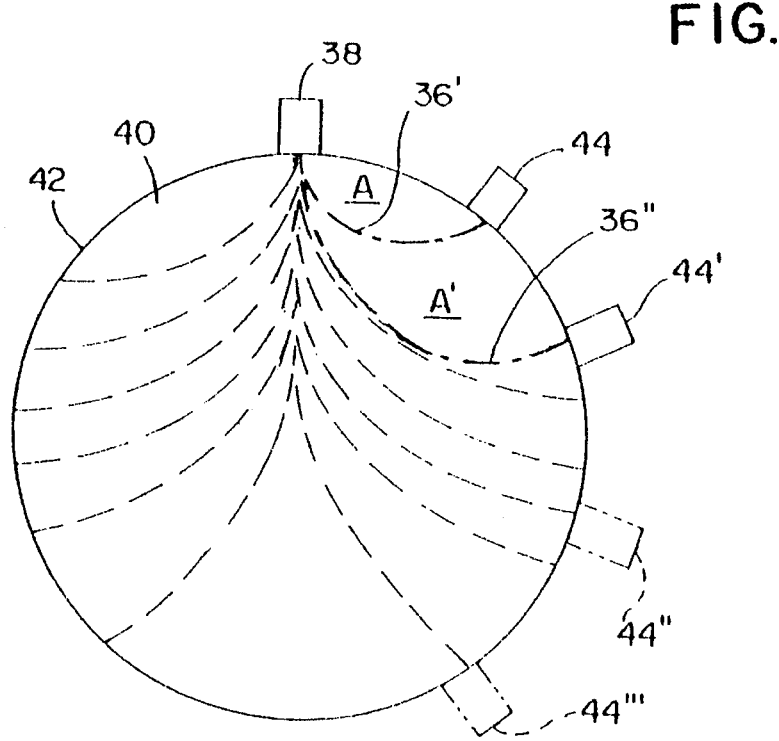
FIG. 3

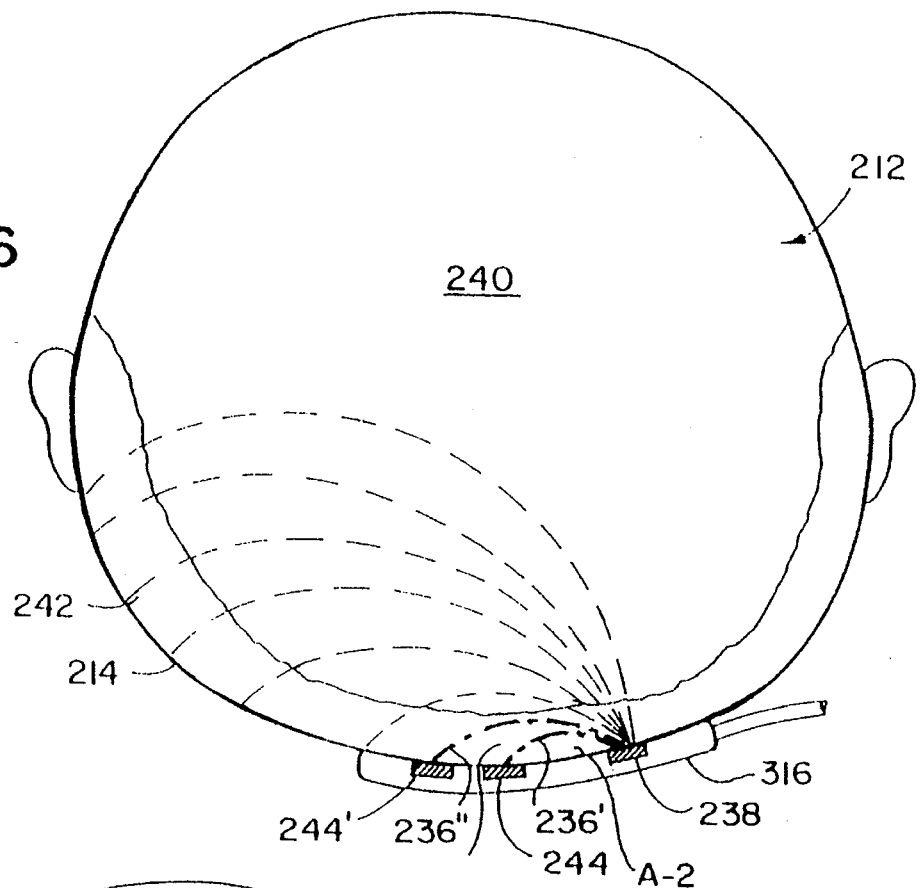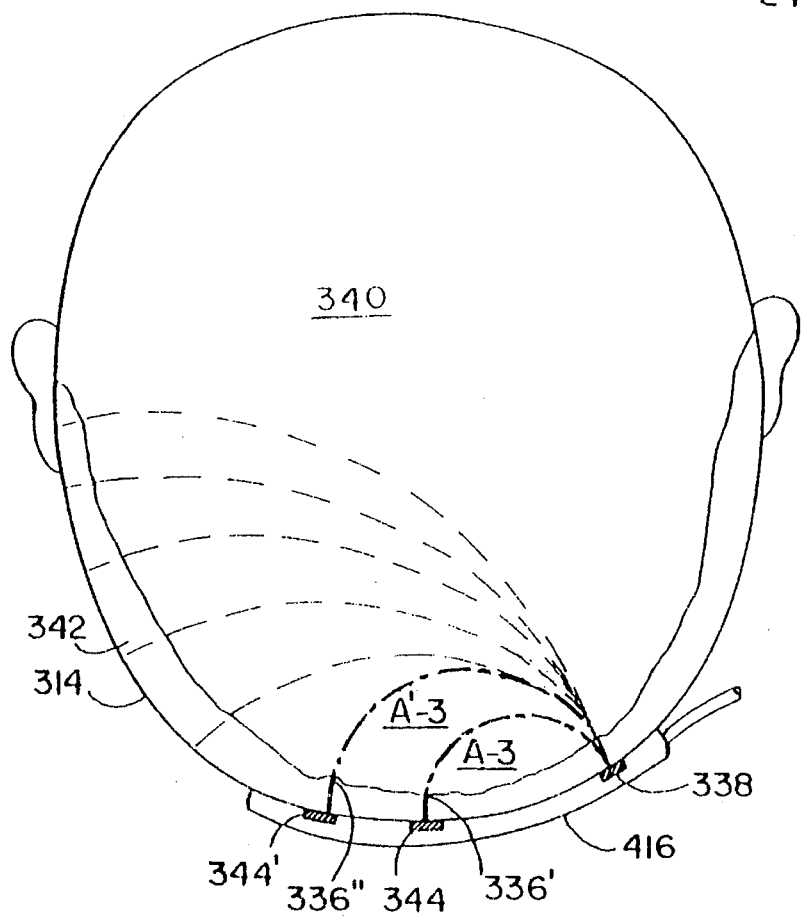

METHOD AND APPARATUS FOR SPECTROPHOTOMETRIC CEREBRAL OXIMETRY AND THE LIKE

This is a continuation of application Ser. No. 08/069,096 filed on May 28, 1993, abandoned.

FIELD OF THE INVENTION

This invention relates generally to bioelectronic medical examination apparatus, and more particularly to the type of such apparatus which operates on spectrophotometric principles, particularly by use of electromagnetic energy in the visible and near infrared range. Still more particularly, the invention relates to apparatus of the foregoing kind which is used to obtain clinical examination data from the brain, particularly the human brain, by means of an electro-optical sensor placed on the forehead of the patient, and especially to the determination of cerebral hemoglobin oxygen saturation in this manner.

BACKGROUND

In our earlier U.S. Pat. No. 5,139,025, and in subsequent U.S. Pat. No. 5,217,013, assigned to the same assignee, various sensor configurations and structures are disclosed for use in spectrophotometric clinical examination apparatus, particularly the cerebral oxygen saturation monitor developed by Somanetics Corporation, of Troy, Mich., which uses electro-optical components mounted in such a sensor to emit light energy of selected wavelengths and project the same through brain tissue located behind the torehead by transmissivity through the epidermal layers and underlying bone of the frontal skull, and to detect resultant light energy at certain locations spaced laterally from the point of light introduction by certain predetermined distances. In the first such patent, a relatively rigid "hard" sensor configuration is disclosed which is principally suitable for use on generally flat or very soft, compliant surfaces and media, while in the second such patent a flexible, compliant sensor is disclosed which is suitable for use on various curved surfaces, to which it may be manually conformed, such as for example the human forehead.

As indicated above, the lateral distance between the light source and detectors used in such sensors is of considerable importance, since such distances in effect determine the depth to which the interrogating light spectra will penetrate the underlying physiological tissue, at least to the extent that sufficient resultant light is detectable by the sensors to allow for processing and analysis which will yield meaningful data as to the state, condition, or other such attributes of the internal tissue sought to be analyzed. Prior patentees have also referred to this principle, or effect, at least in one way or another; for example, F. Jobsis refers to this in his earlier U.S. Pat. No. 4,223,680, although he appears to primarily attribute the underlying principle or rationale to the belief (not shared by the present inventors) that the interrogating light spectra will traverse the scalp, skull, and "gray matter" of the brain immediately underlying the skull along a rectilinear path, but will be abruptly reflected along another such path by the "white matter" of the brain, with a small amount of the light being directed back to the source but most of it being deflected orthogonally and passing back out of the head through the skull and scalp, etc. a particular distance away from the source. In point of fact, Jobsis categorically asserts in one or more of his patents that an absolute minimum separation distance of 4.25 centimeters exists in all such cases, which must be observed if the "gray matter" is to be traversed by the examining spectra, and which will thus control the operation of all such devices.

As indicated, the present inventors do not share the opinion just stated, and on the contrary have demonstrated that other factors and principles are involved, and that the transmission of light energy of selected spectra through the brain will essentially exhibit the characteristics of transmission through a highly scattering and partially absorptive media, through which an essentially infinite number of randomly varying transmission paths will occur, all of which, as a general matter, defining a theoretical mean optical path which is arcuately curved, and in the simplest case, essentially a circular arc, between the source and any given detection location, with an exponential decrease in the intensity of the light as a function of the length of the path it has followed to any given point spaced laterally from the point of origin.

Further, the present inventors have previously disclosed the advantages of using two different detectors, or detector groupings, located at mutually different distances from the source of light energy, one being considered a "near" detector and the other a "far" detector, so that the optical response data produced by each could be comparatively analyzed and the effects upon the dam produced by the "far" detector (which samples light that has penetrated more deeply into the subject) can be conditioned so as to in effect eliminate from it tile optical response data which is attributable to the skin, bone, and related skeletal tissue and vascularity, etc., thereby producing data which effectively characterizes only the internal (e.g., brain) tissue. For the most part, however, it was previously thought that the "near" detector should be located in very close proximity to the source, for a variety of reasons. This view is also reflected in the aforementioned patents of Jobsis, at least certain of which also show the use of both a "near" and "far" detector in the same sensor, although the specific reasons for doing so are not considered to be very well, or clearly explained in these patents.

SUMMARY OF THE INVENTION

The present invention reassesses the highly important aspect of source-receiver positioning and relative separation in light of more comprehensive assessment of human anatomical variations at the particular area where the spectrophotometric procedures involved in determining cerebral oxygen saturation are to be employed, i.e., the human forehead area, including the skin and other adjacent dermal layers, skull thicknesses, and variations in forehead geometry, i.e., the extent, nature, and relative location of curvature, together with the nature and presence of tissue and biological substance (e.g., vasculature, pooled blood volumes, other liquids, membranes, etc.) which do or may directly underlie the skin and skull in the forehead region under any and all possible conditions, including injury, trauma, etc. On these bases, the invention provides particular new source-receiver positioning for the sensor which serves as the patient-machine interface, in order to best accommodate the aforementioned considerations.

In a particular and preferred embodiment, the invention provides an improved methodology and sensor component geometry for use in examination of the human brain and determination of the prevalent conditional state of human brain tissue within a relatively defined internal volume of such tissue (i.e., on a regional basis), by use of the completely non-invasive and innocuous procedures made available by spectrophotometric-type apparatus.

More particularly, the present invention provides novel improvements in methodology and apparatus for a cerebral spectrophotometric sensor as referred to above by which the resulting optical response data is assured of representing purely intrinsic brain tissue, i.e., without the effects which result from passage of the interrogating light spectra through the structure and substances disposed outwardly of the brain itself, i.e., the skin, skull, etc., as noted above. In a broader sense, the novel concepts underlying the invention may be applicable to anatomical areas other than the brain, as should be borne in mind in considering both the foregoing and the ensuing comments relative to and descriptive of the invention.

Accordingly, one characterization of the novel method and apparatus provided by the invention is as follows. Light of selected wavelengths is introduced into the subject from a source location on the outside of its periphery, and first and second light-detection locations are selected on the outer periphery at points spaced from one another and spaced from the source location by unequal, but preferably comparable and not greatly disproportionate, first and second distances, to thereby define unequal first and second mean optical paths extending between the source and the first and second detection locations. By so doing, one such path may be considered as generally defining an overall internal area which contains the particular internal region to be accessed and examined, while the other such path may be considered as defining a secondary internal area which is located generally within the overall such area but which does not include such particular internal region (notwithstanding the fact that in reality some lesser percentage of photons received at the particular detection location involved will no doubt have actually traversed a certain amount of the tissue within such particular region, each "mean optical path" merely representing the idealized path of the predominant number of photons received at the corresponding detector location). In particular, the last-mentioned ("other") such path is selected so that the said secondary internal area includes not only the full thickness of the overlying tissue, etc. disposed between the outer surface and the interior subject or body to be examined, but also at least a small portion of the physiological substance disposed therebeyond, i.e., within the said particular internal volume. By then detecting light at such first and second detection locations resulting from that introduced at the source and producing signals representative of the light detected at both such locations, the signals so produced may be processed to obtain optical response data which particularly characterizes only the tissue of the particular internal region or volume, substantially without effects attributable to any of the tissue and biological substance located between that internal volume and the outside peripheral surface.

In a still more specific sense, the invention provides methodology and apparatus for the indicated spectrophotometric-type clinical examination equipment in which particular distance and positioning parameters are provided for the light source and detectors which will accommodate substantially all known variations in human anatomical size and shape and all or most likely conditions encountered in trauma centers, operating rooms, etc., while consistently providing data which is representative of only the desired internal tissue volume, and not of the overlying tissue and substances disposed nearer the perimeter or making up the peripheral boundaries of the subject. In one particular preferred embodiment, specific relative source-detector separation distances and geometry are provided for the aforementioned cerebral oximeter and directly related apparatus.

BRIEF DESCRIPTION OF THE DRAWINGS

FIG. 1 is a pictorial view illustrating the general environment and structure involved in a preferred embodiment of the invention;

FIG. 2 is a front view of exemplary sensor typifying those previously an used in such applications;

FIG. 3 is a pictorial plan view generally illustrating mean optical path distribution extending from a source to various sensor positions on the perimeter of an idealized highly scattering medium;

FIG. 6 is a second pictorial sectional view representing the human head and showing a second source-detector position arrangement illustrating certain aspects of the invention; and FIG. 7 is a third pictorial sectional view representing the human head and showing a third source-detector position arrangement illustrating certain aspects of the invention.

DESCRIPTION OF PREFERRED EMBODIMENTS

Figure 4:
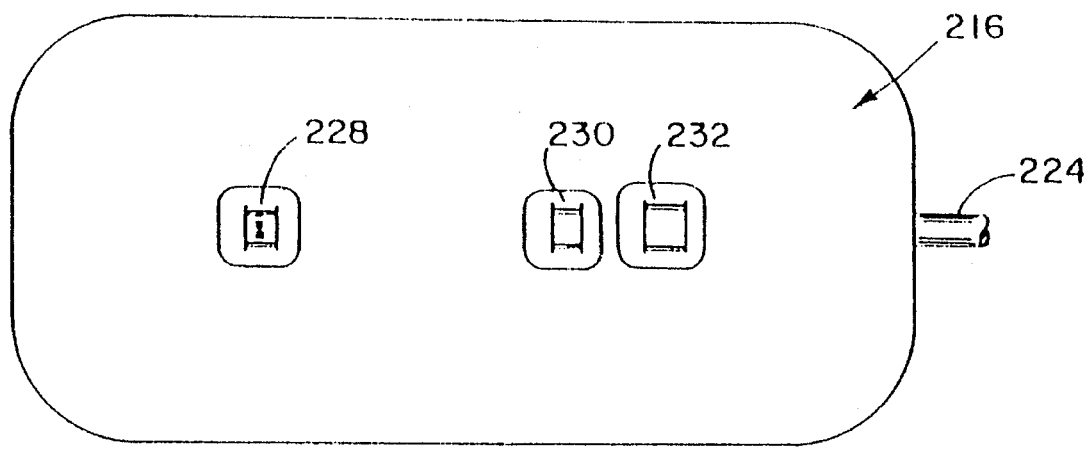
FIG. 4 is an enlarged front elevational view of a sensor in accordance with the present invention.

Referring now to FIG. 1, an illustrative system 10 for practice of the invention includes a subject 12, which in this preferred example is a human being upon whose forehead 14 is disposed a sensor 16 that includes an electro-optical source to provide the desired examination wavelengths and various receivers to detect resultant light after the same has passed through the patient's forehead and ;portions of the brain. The corresponding electrical signals for operating the sensor 16 are supplied by and coupled to a spectrophotometric apparatus 18 which, in the preferred embodiment, is configured as the aforementioned cerebral oximeter, referred to and described generally in co-pending U.S. patent application Ser. No. 08/006,705, filed Jan. 21, 1993, and in a more particular sense as exemplified by the Model 3100 cerebral oximeter developed by Somanetics Corporation, of Troy, Mich. As will be apparent, the apparatus 18 essentially comprises an appropriately-programmed microcomputer or "personal computer" 20 having a monitor or visual display 22, there being an electrical cable 24 extending from the sensor to the apparatus 20 which preferably includes a small amplifier 26 disposed at a predetermined distance from the subject 12 to provide for both optimal safety considerations and detection signal strength for enhanced processing capability.

An exemplary earlier form of the sensor 16 is illustrated in FIG. 2, wherein it is designated by the numeral 116. Basically, this device may be considered to be essentially the same as that illustrated and described in patent application Ser. No. 711,452, filed Jun. 6, 1991, (now U.S. Pat. No. 5,217,013) which in essence operates generally in accordance with prior U.S. Pat. No. 5,139,025, both of which are assigned to the assignee of this application. As such, the sensor 116 includes a source 128, a first or "near" detector 130, and a second or "far" detector 132, all mounted in a convenient body 134 that is preferably sufficiently flexible and compliant as to be conformable to the actual forehead shape of each particular patient by light manual pressure. It is to be noted that the "near" detector 130 shown in the embodiment of FIG. 2 is in fact positioned very near sensor 128, and in accordance with the aforementioned co-pending application Ser. No. 711,452, the optimum such distance for this separation is described as being in the range of about 8 millimeters. In that configuration, the "far" detector 132 is described as preferably being approximately 23 millimeters from source 128.

As noted previously, FIG. 3 illustrates in a generalized, pictorial sense the distribution of different mean optical paths 36 of light from a source 38 introduced into a highly scattering medium 40 disposed within a perimeter 42. As generally depicted in this figure, each of the mean optical paths 36 is arcuately-shaped, and may be considered as a generally circularly-shaped segment in an idealized, illustrative sense, although more generally being described as "banana-shaped" or "canoe-shaped" in technical literature. Consequently, receivers 44, 44' located at different positions along the perimeter 42 will receive the introduced light spectra along differently-located and differently-curved mean optical paths 36', 36", and it will be apparent that each such path in effect defines a different area (designated A, A' inside perimeter 42, area A being within the totality of area A' but distinguishable therefrom). In a three-dimensional subject, the mean optical paths 36', 36" would in fact constitute a family of mutually adjacent such arcuate segments, and the areas A, A' would in fact constitute internal volumes with arcuately-shaped, somewhat spherical, ovoid sides. Of course, other particular sensor placements, as shown in phantom at 44" and 44''', would have correspondingly longer mean optical paths disposed between them and source 38 defining other and progressively larger such internal areas and corresponding volumes.

Figure 5:
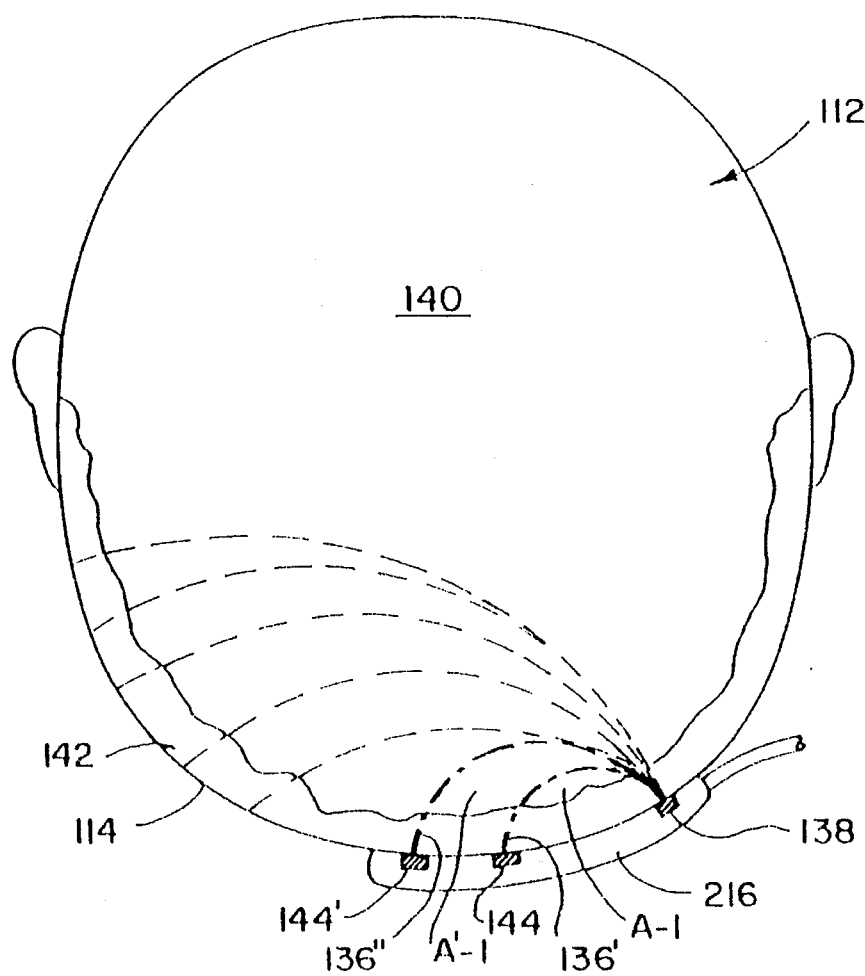
FIG. 5 is a first pictorial sectional view representing the human head and showing a first source-detector position arrangement illustrating certain aspects of the invention.

With reference now to FIGS. 5, 6 and 7, the analogy to the example shown in FIG. 3 will be more apparent, and its significance more readily appreciated. More particularly, each of these three figures represents a cross-section of a simplified human cranium, taken along a plane passing through the forehead 14. In each case, certain variations are shown in a pictorial schematic sense that occur randomly in various human populations, including differing sizes and degrees of roundness or circularity in the forehead region, and differing thicknesses of skin, skull, and underlying tissue, which are collectively represented by the thickness of the irregular arcuate wall denoted by the numeral 142, 242, 342 in FIGS. 5, 6 and 7, respectively, and referred to collectively herein as the "peripheral wall" (in the case of the brain and similarly-situated organs) or "overlying tissue structure" (in the case of other internal organs) or, in either case, simply the peripheral extremity. Thus, while shown simplistically as a single area in these figures, but in fact representing a plurality of complex biological structures are in fact represented, as mentioned at various points hereinabove.

More particularly, the head 112 shown in FIG. 5 (representing a typical case) has a somewhat broadly rounded forehead 114 and a "peripheral wall" 142 of a nominal thickness. With an electro-optical sensor 216 applied to the forehead area, a pair of circularly-shaped mean optical paths 136' and 136" are produced, which may be analogized to the generally corresponding paths 36' and 36" of FIG. 3, discussed above. As a result, a first internal area A-1 is produced between the source 138 and the "near" detector 144, a second such area A'-1 being similarly produced between the source and the "far" detector 144'. As may be observed, the "near" area A-1 does include a moderate amount of the internal (brain) tissue, designated by the numeral 140, although not as much as the area A'-1.

Considering FIGS. 6 and 7, it may be noted that the head 212 in FIG. 6 is larger and much more broadly rounded than that of skull 112 shown in FIG. 5, with a flatter forehead 214. On the other hand, the skull 312 of FIG. 7 is smaller and more elliptical, with a more sharply curved forehead area 314 than the corresponding examples shown in FIGS. 5 and 6. In addition, the sensor 416 shown in FIG. 7 is somewhat more elongated than the sensors 216 and 3 14 shown in FIGS. 5 and 6. As a result, the shorter mean optical path 236' of FIG. 6 does not in fact enter the brain tissue 240 at all, and even the longer mean optical path 236" hardly enters the brain tissue. Therefore, the volume A-2 sampled by the near detector 244 is disposed entirely within the "peripheral wall" 242, and indeed even the larger volume A'-2 sampled by the far detector 244' primarily consists of the peripheral wall constituents rather than brain tissue 240. Basically, a somewhat opposite condition is illustrated in FIG. 7, in which both of the mean optical paths 336', 336" extend substantially into the brain tissue 340, and the sampled volumes A-3, A'-3 both include substantial amounts of the brain tissue 340, particularly the volume A'-3.

In the preferred processing of output signals from the electro-optical detectors of the sensor, referred to in more detail in earlier U.S. Pat. No. 5,139,025 and co-pending application Ser. No. 08/006,705, filed Jan. 22, 1993, the characteristics of the tissue within the smaller internal area defined by the output signals from the "near" detector are in effect subtracted from the characteristics of the larger internal volume defined by the output from the "far" detector, thereby producing resultant data which is characteristic of a particular internal volume disposed well beyond the peripheral wall, particularly where the "peripheral wall" or "overlying tissue structure" is essentially the same in thickness and characteristic tissue in the area immediately adjacent both such detectors, which is an important consideration within the purview of the invention. That is, with the extensive variations in particular anatomical structure actually encountered between humans of different ethnicity, size, skull thickness, age, vascular structure, etc., variations in the "peripheral wall" or "overlying tissue structure" will certainly occur, not only from one patient to the next, but even in the same patient. Also, as indicated above, significant differences in the degree and type of forehead curvature, etc. are to be expected, rather than the opposite.

Accordingly, as such differences are considered in further detail and explored further, it ultimately becomes clear that the "near" detector should more properly be located closer to the "far" detector than to the source, particularly in the case of spectrophotometric examination of brain tissue, e.g., as applied to a cerebral oximeter as mentioned above, notwithstanding the fact that this is to a considerable extent contrary to prior thinking in this regard. That is, the only way to make certain that the resultant data ultimately obtained does in fact characterize primarily or exclusively internal brain tissue rather than peripheral, epidermal or intervening anatomical substances or structures is to try to make certain that the smaller of the two internal volumes sampled (i.e., that resulting from the "near" receiver output) includes at least the entire thickness of the skin, skull, etc. constituting the "peripheral wall" or boundary, throughout all of the anticipated anatomical variations which may be encountered in peoples from around the world, and in addition, includes at least a minimal amount (and preferably a significant amount) of internal brain tissue within the smaller of the two volumes so sampled.

In point of fact, the present invention recognizes that it is very desirable to have the smaller such internal volume be relatively large in relation to the other such volume, i.e., be almost as large as the other such volume, so that both mean optical paths lie relatively close to one another. By so doing, it becomes much more likely that the thickness and composition of the intervening adjacent biological structure (i.e., the "peripheral wall" or "overlying tissue structure") traversed by photons received at both the "near" and "far" detectors will be the same, or substantially so, and as stated above this is an important factor in achieving accurate results.

At the same time, it is also important to have the "far" detector located at a sufficient distance from the "near" detector to ensure that a significantly different internal volume is sampled by that detector, so that the difference will represent and characterize a meaningfully distinct internal volume, and thereby reliably represent strictly internal tissue situated well within the brain itself. Nonetheless, it must be recognized that the farther either such detector is placed from the source, the more difficult it is to detect sufficient resultant light energy to afford reliable and meaningful processing, bearing in mind that the selected examination wavelengths provided by the source must be accurately representative of those whose selective absorption by reduced and oxygenated hemoglobin is accurately known, and that the amount of power used to generate the resultant light must be maintained at safe and relatively low levels.

With all of the foregoing factors in mind, studies and testing have led to the final conclusion that, for human brain examination, and particularly for cerebral oxygen determination, the "near" detector should be located at least about 20–25 millimeters away from the source, and preferably somewhat further than that, i.e., about 30 millimeters. At the same time, the "far" detector should be positioned at least about 5 to 10 millimeters distant from the "near" detector to guarantee that a distinguishable and different internal tissue volume is in fact sampled by the second such detector, while also assuring that significant detection signal strength will be present. Thus, while a certain range of preferred such positions is potentially present, a specific example of a most preferred such arrangement places the "near" detector at a point 30 millimeters distant from the source, with the "far" detector positioned 10 millimeters beyond, i.e., at a point 40 millimeters away from the source (which is presently considered the maximum such distance which is useful as a practical matter, with commercially available and economically feasible components). This relationship is illustrated in FIG. 4, wherein an enlarged sensor 216 is shown which has its "near" detector 230 disposed at a point which is clearly much further away from its source 228 than is true of the relationship shown in FIG. 2, wherein the "near" detector 130 is clearly much closer to source 128. In point of fact, the "near" detector 230 in the sensor 216 of FIG. 4 is located at a point analogous to the location of the "far" detector 132 of previous sensor 116 shown in FIG. 2, while the "far" detector 232 of sensor 216 in accordance with the invention is actually disposed even further away from its corresponding source than the "far" detector 132 of earlier sensor 116.

In view of the aforementioned particular factors and their corresponding significance, the most preferred embodiment of the present invention utilizes a larger detector (photodiode) for the "far" position than that used at the "near" position, so as to increase the likely amount of photon reception by the "far" detector. Of course, within commercially available components there are at least a certain number of different sizes of photodetectors available, notwithstanding cost variations, and whereas prior sensors were implemented by use of photodiodes having an effective surface area of 7.5 square millimeters for both the near and far detector, in accordance with the present invention the far detector is preferably implemented by use of a component essentially twice the size of that previously used at this location, i.e., a 15 square millimeter photodiode. In other respects, the physical structure of the preferred sensor configuration 216 in accordance with the invention is in accordance with that disclosed and claimed in co-pending application Ser. No. 08/065,140 filed May 20, 1993), commonly owned herewith, since that structure provides significant advantages over others used heretofore. Of course, the particular examination spectra emitted by the source remains the same (i.e., approximately 760 nm and 803 nm), and the source should therefore be implemented in the same manner as that referred to in prior patents and/or applications commonly owned herewith, i.e., by wavelength-specific light-emitting diodes.

It is believed that the significant advantages provided by the present invention will be apparent to and appreciated by those skilled in the art upon consideration of the foregoing disclosure, and it is to be noted once again that an underlying concept is advanced which is specifically different from those addressed by the prior state of the art, notwithstanding the superficially similar attributes. It is to be understood that the foregoing detailed description is merely that of certain exemplary preferred embodiments of the invention, and that numerous changes, alterations and variations may be made without departing from the underlying concepts and broader aspects of the invention as set forth in the appended claims, which are to be interpreted in accordance with the established principles of patent law, including the doctrine of equivalents.

The embodiments of the invention in which an exclusive property or privilege is claimed are defined as follows:

1. A method of non-invasively examining by optical response a physiological substance located within a particular internal region inside an animate test subject having a peripheral extremity of specifically indeterminate thickness disposed generally between said internal region and the outer periphery of the subject, comprising the steps:

introducing light of selected wavelengths into said subject from a source location outside said peripheral extremity;

selecting at least first and second light-detection locations on said outer periphery at points spaced from one another and spaced from said source by unequal first and second distances to thereby define a first mean optical path extending between said source and said first detection location and a second mean optical path of a length different than that of said first mean optical path and extending between the source and said second detection location;

selecting said second path to generally define a primary internal area which contains said particular internal region and selecting said first optical path to generally define a secondary internal area which is located generally within said primary internal area but which is substantially separate from said particular internal region, and particularly selecting said first path to include the full thickness of a predetermined typical such peripheral extremity plus at least a small portion of the said physiological substance therebeyond;

detecting the light resulting from said introduced light at said first and second detection locations, producing signals representative of such detected light, and processing said signals to obtain optical response data which particularly characterizes selected attributes of said physiological substance within said particular internal region substantially without effects attributable to said secondary internal volume.

2. The method of claim 1, wherein said physiological substance comprises a highly scattering and partially absorptive media and said mean optical paths comprise arcuate curves.

3. The method of claim 1, including selecting said second optical path to traverse a generally predetermined internal brain area.

4. The method of claim 1, in which said step of selecting said first detection location comprises locating a detector not less than about twenty millimeters from the place at which said light is introduced into said subject from said source.

5. The method of claim 1, in which said step of selecting said second detection location includes locating a detector not less than about thirty millimeters from the place at which said light is introduced into said subject from said source.

6. The method of claim 5, in which said step of selecting said first detection location comprises locating a detector not less than about twenty millimeters from the place at which said light is introduced into said subject from said source.

7. The method of claim 1, in which said step of selecting said first detection location comprises locating a detector at about twenty-five to thirty millimeters from the place at which said light is introduced into said subject from said source.

8. The method of claim 1, in which said step of selecting said second detection location includes locating a detector at about thirty to forty millimeters from the place at which said light is introduced into said subject from said source.

9. The method of claim 8, in which said step of selecting said first detection location comprises locating a detector at about twenty-five to thirty millimeters from the place at which said light is introduced into said subject from said source.

10. In a method of appraising the internal structure of selected organic bodies and materials, wherein electromagnetic energy is used as an investigative media by passing it through both internal portions of said bodies and materials and overlying tissue structures and quantitative data is produced from such energy which characterizes the composition, condition and/or physiology of a particular area of said internal structure, and wherein a source and at least two receivers are used to send electromagnetic energy of selected wavelengths into and through the selected body or material and receive such energy at at least two separate and mutually-spaced external locations including a first location disposed at least somewhat nearer to said source than a second location, and the resulting energy so received is quantified to obtain characteristic response data values, the improvement comprising:

using as one of said locations a point at which the said energy there received and its corresponding data values characterize primarily said particular area of internal structure, and using as the other of said locations a point at which the energy there received and its corresponding data values characterize both said overlying tissue structure and at least a minimal amount of said internal structure which is located inwardly of said overlying structure, whereby quantified response data valuations are obtained which are assured of characterizing the internal structure at said particular area within said body or material on a generally intrinsic basis and which are independent of characteristics attributable to said overlying tissue structure.

11. The improvement according to claim 10, in which said step of using a source and at least two receivers is carried out by physically carrying said source and receivers on a single sensor member with said source and receivers disposed at measured distances from one another.

12. The improvement according to claim 10, in which said bodies and materials are the human head and brain, respectively, and said step of receiving energy at said first location includes disposing both of said receivers at points on the forehead located at least about twenty millimeters from another such point at which said energy is introduced into said head and brain.

13. The improvement according to claim 10, in which said bodies and materials are the human head and brain, respectively, and said step of receiving energy at said first location includes disposing at least one of said receivers at a point on the forehead located at about twenty-five to thirty millimeters from another such point at which said energy is introduced into said head and brain.

14. The improvement according to claim 13, in which said step of using a source and at least two receivers is carried out by physically carrying said source and receivers on a single sensor member with said source and receivers disposed at measured distances from one another.

15. Apparatus for obtaining optical response data from discrete organic bodies which is exclusively representative of internal tissue located inside the boundaries of such bodies, comprising in combination:

at least one optical sensor including a source and at least two receivers adapted for placement in optically coupled relation with selected areas on said body and adapted to pass light of selected wavelengths from said source to said receivers through such body;

means for holding said source and receivers in predetermined spatial relation while optically coupled to said selected areas of said body;

said at least two receivers including a first receiver for receiving such light from said source at a first position with respect to s;aid light source as well as a second receiver for receiving such light at a second position located at least somewhat further away from said source than said first position, and for producing corresponding signals representative of data values for each such position which are correlated with said selected wavelengths, both said first and second positions being located so that the light received at each has traversed substantially similar portions of said boundaries and a certain amount of said internal tissue but said second position being located so that the light received there has traversed more of said internal tissue that the light received at said first location; and means for receiving said signals and producing data values therefrom which characterize the light received at one such position as a function of corresponding light received at the other such position, such that the resulting data values comprise representations of intrinsic characteristics of said internal tissue and are free of optical effects resulting from factors attributable to passages of said light through said boundaries, said first receiver being positioned at a location which is not closer than about twenty millimeters from the location of said source.

16. Apparatus for obtaining optical response data from discrete organic bodies which is exclusively representative of internal tissue located inside the boundaries of such bodies, comprising in combination:

at least one optical sensor including a source and at least two receivers adapted for placement in optically coupled relation with selected areas on said body and adapted to pass light of selected wavelengths from said source to said receivers through such body;

means for holding said source and receivers in predetermined spatial relation while optically coupled to said selected areas of said body;

said at least two receivers including a first receiver for receiving such light from said source at a first position with respect to said light source as well as a second receiver for receiving such light at a second position located at least somewhat further away from said source than said first position, and for producing corresponding signals representative of dam values for each such position which are correlated with said selected wavelengths, both said first and second positions being located so that the light received at each has traversed substantially similar portions of said boundaries and a certain amount of said internal tissue but said second position being located so that the light received there has traversed more of said internal tissue than the light received at said first location; and means for receiving said signals and producing data values therefrom which characterize the light received at one such position as a function of corresponding light received at the other such position, such that the resulting data values comprise representations of intrinsic characteristics of said internal tissue and are free of optical effects resulting from factors attributable to passages of said light through said boundaries, said second receiver being positioned at a location which is about thirty to forty millimeters from the location of said source.

17. Apparatus according to claim 16, in which said first receiver is positioned at a location which is not closer than about twenty millimeters from the location of said source.

18. In a method of conducting non-invasive clinical patient examinations of brain tissue by in vivo spectrometry, wherein selected wavelengths of electromagnetic energy are introduced into the brain through the scalp and skull at a first location and resultant amounts of such energy are received at a predetermined number of second locations after transmission back out through the scalp and skull, the improvement in obtaining resultant data which characterizes only brain tissue, comprising:

determining the approximate position for one of said second locations where the resultant energy received will have traversed the scalp, skull and at least a minimal amount of said brain tissue in passing from said first location to said one second location;

determining the approximate position for another of said second locations where the resultant energy received will have traversed the scalp, skull and an amount of said brain tissue greater than said at least minimal amount of brain tissue;

quantifying said resultant amounts of energy received at both said one and said other second locations; and conditioning the said quantifications of resultant energy received at said one and said other locations by contrasting one with the other such that resultant data is obtained which generally characterizes the difference between said at least minimal amount of brain tissue and said greater amount of brain tissue.

19. The method improvement defined in claim 18, wherein said steps of determining position for said second locations includes using a representative measure of skull thickness and skull curvature at a predetermined area of the skull.

20. The method improvement defined in claim 19, wherein said predetermined area of the skull is the forehead.

21. The method improvement defined in claim 20, wherein said one and said other second locations are determined to be more closely adjacent one another than either is to said first location.

\* \* \* \* \*

UNITED STATES PATENT AND TRADEMARK OFFICE
CERTIFICATE OF CORRECTION

PATENT NO. : 5,482,034
DATED : January 9, 1996
INVENTOR(S) : Lewis et al.

page 1 of 2

It is certified that error appears in the above-indentified patent and that said Letters Patent is hereby corrected as shown below:

Column 1, line 33
"torehead" should be --forehead--.

Column 4, line 10
After "previously" delete "an".

Column 4, line 38
";portions" should be --portions--.

Column 5, line 4
Delete "co-pending".

Column 6, line 10
"3 14" should be --314--.

Column 10, line 41
"s;aid" should be --said--.

Column 10, line 53
"that" should be --than--.

Column 10, line 60
"passages" should be --passage--.

UNITED STATES PATENT AND TRADEMARK OFFICE
CERTIFICATE OF CORRECTION

PATENT NO. : 5,482,034
DATED : January 9, 1996
INVENTOR(S) : Lewis et al.

It is certified that error appears in the above-indentified patent and that said Letters Patent is hereby corrected as shown below:

Column 11, line 15
    "dam" should be --data--.

Column 11, line 31
    "passages" should be --passage--.

Abstract, line 26
    "volume," should be --volume.--.

Signed and Sealed this

Seventeenth Day of September, 1996

Attest:

BRUCE LEHMAN

*Attesting Officer*      *Commissioner of Patents and Trademarks*